(12) United States Patent
Yan

(10) Patent No.: US 7,995,703 B2
(45) Date of Patent: Aug. 9, 2011

(54) METHOD FOR CONTROLLING X-RAY EXPOSURE IN X-RAY CT SYSTEM

(75) Inventor: Xiongwei Yan, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 155 days.

(21) Appl. No.: 12/342,434

(22) Filed: Dec. 23, 2008

(65) Prior Publication Data

US 2009/0168951 A1 Jul. 2, 2009

(30) Foreign Application Priority Data

Dec. 29, 2007 (CN) .......................... 2007 1 0308137

(51) Int. Cl.
*H05G 1/10* (2006.01)
*H05G 1/34* (2006.01)
*G01N 23/083* (2006.01)
(52) U.S. Cl. .......................................... 378/16; 378/110
(58) Field of Classification Search .................. 378/4, 5, 378/8, 16, 91, 101, 108–117, 205, 210
See application file for complete search history.

(56) References Cited

U.S. PATENT DOCUMENTS

| | | | |
|---|---|---|---|
| 4,398,302 A | 8/1983 | Pfeiler | |
| 5,379,333 A * | 1/1995 | Toth | 378/16 |
| 5,400,378 A * | 3/1995 | Toth | 378/16 |
| 5,452,338 A | 9/1995 | Granfors et al. | |
| 5,457,724 A * | 10/1995 | Toth | 378/4 |
| 5,696,807 A * | 12/1997 | Hsieh | 378/109 |
| 5,923,722 A | 7/1999 | Schulz | |
| 6,350,985 B1 | 2/2002 | Rodricks et al. | |
| 6,501,828 B1 * | 12/2002 | Popescu | 378/150 |
| 6,990,171 B2 * | 1/2006 | Toth et al. | 378/16 |
| 7,026,608 B2 | 4/2006 | Hirai | |
| 7,119,327 B2 | 10/2006 | Spahn et al. | |
| 7,236,572 B2 | 6/2007 | Maschke | |
| 7,404,673 B2 | 7/2008 | Hornig | |
| 7,428,294 B2 | 9/2008 | Spahn | |
| 2003/0185343 A1 * | 10/2003 | Horiuchi | 378/108 |
| 2005/0089136 A1 * | 4/2005 | Toth et al. | 378/16 |

\* cited by examiner

*Primary Examiner* — Anastasia Midkiff
(74) *Attorney, Agent, or Firm* — Armstrong Teasdale LLP

(57) ABSTRACT

A method for controlling automatic X-ray exposure in an X-ray CT system includes establishing a correspondence table or function relationship between a ratio factor and an offset of a geometrical center of a scanned section, wherein the ratio factor represents a ratio of the projection area value when the geometrical center of the scanned section of a subject deviates from a rotation center to the standard projection area value when the geometrical center of the scanned section of the subject locates at the rotation center, scout scanning the subject, and calculating a "measured projection area value" and Projection Measure based on the scout scan data, calculating the offset of the geometrical center of the scanned section from the rotation center, substituting the offset into the correspondence table or function relationship to obtain a corresponding ratio factor, calculating the standard projection area value based on the ratio factor and the measured projection area value, and automatically determining by an automatic exposure function a tube current value required for exposure based on the calculated standard projection area value, the Projection Measure.

12 Claims, 8 Drawing Sheets

METHOD FOR CONTROLLING X-RAY EXPOSURE IN X-RAY CT SYSTEM

CROSS REFERENCE TO RELATED APPLICATIONS

This application claims the benefit of Chinese Patent Application No. 200710308137.3 filed Dec. 29, 2007, which is hereby incorporated by reference in its entirety.

BACKGROUND OF THE INVENTION

The embodiments described herein relate to the exposure of X-rays, and in particular, to a method for controlling the X-ray exposure in a CT system during a scanning process.

An X-ray CT system emits X-rays to a subject (patient), detects by a detector the X-ray absorption coefficient in such human body tissues as organs, blood and gray matter, and processes (reconstructs) said absorption coefficient by a computer to provide an image (tomographic image) of the sectional plane (slice plane) of the area to be examined.

A doctor diagnoses the patient's condition on the basis of the tomographic image of a predetermined area to be examined that is reconstructed by the X-ray CT system. For this purpose, the image quality of the reconstructed tomographic image must fine enough to distinguish the difference of the X-ray absorption coefficients of the human tissues and to match with the purpose of the examination. To obtain such image quality, the image noise shall be reduced, i.e. to reduce the image noise and obtain high quality tomographic image, the amount of X-rays transmitted by the subject and detected on the detector must be large. As a result, in order to obtain enough transmitted X-rays on the detector, the amount of X-rays emitted to the subject must be large.

However, increasing the amount of X-rays emitted to the subject to improve the image quality will result in a undesired increase in the exposure of the patient to X-ray, so in actual practice, real-time control is required so that the amount of X-rays emitted from the X-ray tube is the minimum amount necessary to get the required image quality.

The amount of X-rays emitted from the X-ray tube is controlled by the current transferred to the X-ray tube (hereinafter referred to as tube current). Conventional X-ray CT system usually provides a function of controlling tube current to achieve said minimum X-ray emission (including automatic tube current control function). As shown in FIG. 1, the automatic tube current control function in such conventional X-ray CT system includes the following steps: step 100, performing a scout scan on a predetermined area of the subject in a predetermined direction to obtain desired data of the scout scan; step 101, analyzing and processing the data obtained in step 100 so as to calculate the eccentricity and the value of the projection area of an elliptic slice of the area to be examined at the scout scan position (the Projection Measure reflects the length of the long axis or short axis of the elliptic slice, the eccentricity can be derived from the projection area value and the Projection Measure), said slice being almost an ellipse; step 102, calculating the tube current for exposure on the basis of the Projection Measure, projection area value, noise desired by the doctor as well as the intrinsic parameters of the system. The system performs exposure and axial scan on the slice based on the calculated tube current. In other words, the tube current mA in automatic tube current control is a function of the projection area Pa and Projection Measure as the following: mA=f (Pa, Projection Measure, desired image noise value, system parameters). Then it can be appreciated that, when the X-ray CT system is determined, the tube current is mainly determined by the Projection Measure obtained from scout scan and the projection area value of the slice, so only accurately calculated Projection Measure and projection area value of the slice can yield tube current that really matches the slice to be scanned.

However, in actual application, the center of the subject being scanned moves up and down with the scan bed, thus deviating from the rotation center of the scan device of the X-ray CT system, and so the data obtained from scout scan is not accurate, resulting in a discrepancy between the calculated projection area value of the slice and the real projection area value of the slice. The final result is that the calculated tube current is either too large or too small, causing the patient under examination either to receive too much X-rays and get hurt or to receive too little and leave the doctor unable to accurately determine the state of an illness. For example, as shown in FIG. 3, a patient lies on a bed deviating from the rotating center ISO of the CT system, and 0 degree and 180 degree scout scans are carried out, with the doctor still using said automatic tube current control function to scan the patient. Even if in the same scan position, the tube current value and the image noise value of axial scan results may differ by a large extent. Clinical practice often has such results: the tube current value of axial scan after 180 degree scout scan is twice that after 0 degree scout scan. Too large tube current value will bring extra harm to the patient. Such tube current control function may produce contradictory results, making it difficult for the doctor to promote the clinical application of the tube current control function.

BRIEF DESCRIPTION OF THE INVENTION

In one aspect, a tube current control method is provided for eliminating the influence on the projection area of a slice by the deviation of the patient center from the rotation center of the CT system, thereby improving the stability and robustness of the exposure system in an X-ray CT system.

In another aspect, a method for controlling the automatic X-ray exposure in an X-ray CT system is provided. The method includes establishing a correspondence table or function relationship between a ratio factor r and the offset Cy of the geometrical center of the scanned section, wherein the ratio factor r represents a ratio of the projection area value under the situation where the geometrical center of the scanned section of the subject deviates from the rotation center to the standard projection area value under the situation where the geometrical center of the scanned section of the subject locates at the rotation center. The subject is then scout scanned and the "measured projection area value" and the Projection Measure are calculated based on the data obtained in the scout scan. The method also includes calculating the offset Cy of the geometrical center of the scanned section from the rotation center, and substituting the offset Cy into the correspondence table or function relationship to obtain its corresponding ratio factor r. The standard projection area value is then calculated based on the ratio factor r and the measured projection area value, and the tube current value required for the exposure is automatically determined using an automatic exposure function based on the calculated standard projection area value, Projection Measure and other system parameters and carrying out the exposure.

The calculation of the offset Cy can be carried out by supposing that the human body is equivalent to a homogenous water body; and then deriving the short axis b of the scanned section of the human body from the following formula:

$$b = k * pm/2,$$

wherein pm is said Projection Measure, k is a constant. And the offset Cy is equal to the sum of the short axis b of the scanned section and the distance of the scan bed from the rotation center.

The short axis b of the scanned section can be obtained from the following fitting formula:

$$b=f(pm)=a0+a1 \times pm+a2 \times pm^2+a3 \times pm^3+\ldots$$

wherein a0, a1, a2 and a3 are coefficients in the polynomial.

The calculation of the offset Cy can also be carried out by first performing segmentation on an image of the previous section to determine the contour of the scanned section of the human body, and then calculating the average value of the Y-axis coordinates of all the pixel points on the image of section contour, with the average value being taken as the offset Cy of the scanned section.

The calculation of the offset Cy can further be carried out by collecting all original projection data in the previous axial scan; finding from said projection data the tube rotation angle $\beta_0$ to which the maximum projection value $P(\beta_0)$ corresponds and at which the tube focus and the central point of the patient are in the same horizontal line; and calculating the offset Cy of the scanned section according to the following formula:

$$Cy=L*\cos(\beta 0)$$

wherein L is the distance from the tube focus to the rotation center.

The function relationship between the offset Cy and the ratio factor r can be obtained by simulation scanning an elliptical phantom of which the long axis, the short axis and the offset are respectively a, b and Cy (or a round phantom of which the radius and the offset are R and Cy respectively) to calculate the projection area value pa(0) in the case of the offset Cy being 0 and the respective projection area values pa(Cy) in the cases of the offset Cy being other than 0; calculating the ratio factor r at respective offset Cy; and creating an index table (Cy, r) to describe the correspondence between Cy and r.

The function relationship between the offset Cy and the ratio factor r can be expressed by the following function:

$$r=3.69 \times 10^{-6} \times Cy^2+1.946 \times 10^{-3} \times Cy+0.999$$

In another aspect, a method is provided for controlling the automatic X-ray exposure in the X-ray CT system. The method is carried out in such a situation that a scout scan has been performed on a scan area to obtain the scout scan data of the scanned section and the axial scan of the previous scan has finished but the axial scan of the current slice has not started. The method includes calculating a standard projection area value of the previous slice on the basis of the projection data of the axial scan of the previous slice, and calculating the "measured projection area value" of the previous slice and the "measured projection area value" and Projection Measure of the current slice on the basis of the projection data of the scout scan. The method also includes calculating the ratio factor ra(Cy) of the previous slice on the basis of the standard projection area value and measured projection area value of the previous slice, wherein said ratio factor ra(Cy) of the previous slice is a ratio of the standard projection area value to the measured projection area value. The method also includes predicting the ratio factor of the current slice by using linear interpolation on the basis of the ratio factors of the previous two slices, calculating the predicted standard projection area value of the current slice on the basis of the ratio factor of the current slice and the measured projection area value of the current slice, and automatically determining the tube current value required for the exposing the current slice by the automatic exposure function of the CT system on the basis of the predicted standard projection area value of the current slice, the Projection Measure and related system parameters, and carrying out the exposure.

The standard projection area value of the previous slice can be obtained by calculating the projection area value (pa(i−1, Cy)) of the previous slice at the offset (Cy) and the Projection Measure ($pm_0$) when the tube is at 0 degree on the basis of the scout scan data during the scanning process of the previous slice, wherein Cy is the offset of the patient from the rotation center of the CT system; finding the tube rotation angle ($\beta_0$) to which the maximum projection data value $P(\beta_0)$ corresponds, and thus the Projection Measure ($pm_{90}$) at said rotation angle ($\beta_0$), because at the rotation angle ($\beta_0$), the X-ray at the channel that has a fan-beam flare angle of ($(\pi/2-\beta_0)$) with respect to the central channel passes through the long axis of the scanned elliptical slice; and calculating the standard projection area value (pa(i−1,Cy=0)) of the previous slice at an offset (Cy) of 0 by the following formula:

$$pa(i-1,Cy=0)=pm_0*pm_{90}*S+I,$$

wherein #(i−1) represents the previous slice, S and I are constants.

The ratio factor of the previous slice obtained can be obtained by extrapolation.

The measured projection area value of the current slice is the measured projection area value of the previous slice calculated on the basis of the projection data of the scout scan.

In another aspect, a method is provided for controlling the automatic X-ray exposure in the X-ray CT system. Said method is carried out in the case that the axial scan of the previous slice has been finished but the axial scan exposure of the current slice has not begun. The method includes establishing a function relationship between the automatic tube current mA value and the parallel beam projection area value and the Projection Measure, and calculating the parallel beam projection area value of the previous slice on the basis of the projection data of the axial scan of the previous slice. The method also includes deducing the parallel beam projection area value of the current slice on the basis of the parallel beam projection area value(s) of the previous one or two slices, determining the tube current value mA1 required for partially scanning the current slice on the basis of the deduced parallel beam projection area value of the current slice and other necessary information according to the function relationship, and performing exposure by using said mA1 value with the tube being in the rotation range of [0, $2\gamma_m$], wherein said $\gamma_m$ is half the fan-shaped flare angle of the X-ray beam. The method also includes calculating the actual parallel beam projection area value of the current slice on the basis of the projection data of the current slice where the tube is within the rotation range of [0, $2\gamma_m$], substituting the parallel beam projection area value of the current slice and other system parameters into the function relationship, and determining the tube current value mA2 required for scanning the current slice when the tube is within the rotation range of [$2\gamma_m$, $2\pi$], and performing exposure by using said tube current value mA2 with the tube being within the rotation range of [$2\gamma_m$, $2\pi$].

The method for obtaining the parallel beam projection area includes converting the fan-shaped beam projection into parallel beam projection by interpolation or beam rebinning, performing, by interpolation, equidistant processing on the parallel beam to obtain equidistant parallel beam projection, and calculating the sum of the projection values of all channels of parallel beams with equal interval, and said sum is the parallel beam projection area value The parallel beam projection area value of the current slice is equal to the parallel beam projection area value of the previous slice. The estimated parallel beam projection area value of the current slice and the Projection Measure are substituted into the function relationship to generate a tube current value mA1 required for exposure of the current slice, and the tube current value mA1 is applicable for scanning the current slice only when the tube is within the rotation range of $[0, 2\gamma_m]$.

The actual parallel beam projection area value of the current slice is obtained by first collecting all projection data of the current slice within the tube rotation angle range of $[0, 2\gamma_m]$; finding a group of unique parallel beams which have an angle of $\gamma_m$ with respect to Y-axis, with $\gamma_m$ satisfying:

$$\beta+\gamma=\gamma_m,$$

wherein $\beta$ represents the angle of rotation of the tube, and $\gamma$ represents the fan-shaped flare angle of the beam of a certain channel with respect to the central channel; and calculating the actual parallel beam projection area value of the current slice on the basis of the parallel beams found above.

The embodiments described herein eliminate the influence of the offset of the geometrical center of the scanned section from the rotation center ISO on the calculation of the projection area value. The method of the present invention makes the projection areas calculated proximate to the actual projection area value of a section whether in the case of scout scan at 0 degree, scout scan at 180 degree or scout scan with an offset, thus makes the tube current value required for exposure more proximate to the actual demand, thereby improving the stability and clinical effectiveness of the automatic exposure function and reducing the possibility of the patient receiving too much radiation from over-scanning.

DETAILED DESCRIPTION OF THE INVENTION

Following are detailed explanations of the embodiments for implementing the present invention with reference to the drawings, but the present invention is not limited to said embodiments.

The embodiments described herein facilitate achieving automatic exposure control function having precise and stable tube current value by eliminating the influence of the distance deviation (hereinafter referred to as offset) of the geometrical center of the scanned section of the patient from the rotation center ISO (ISO: isocenter) of the scan gantry of the CT system on the projection area value of a slice obtained in a scout scan. The "patient position" refers generally to the vertical distance from the rotation center ISO of the CT scan gantry to the geometrical center of the scanned section of the patient, namely the above mentioned offset. The examples given below all suppose that the human body is left-right symmetrical and faces up, and are implemented in the case of scout scan at 0 degree.

In a program of the tube current automatic exposure control function, the projection area PA means the sum of the projection values of all channels in a scout scan, the Projection Measure PM means the sum of the projection values of 100 channels which are the maximum.

In the embodiments of the present invention, the automatic exposure control functions and the coefficients therein need to be designed through calibrations. During the design through calibration, all the geometrical centers of the phantoms under examination are in the position of the rotation center ISO. The projection area value of the scanned section that is measured when the subject does not have an offset is defined as the standard projection area value.

Figure 1:
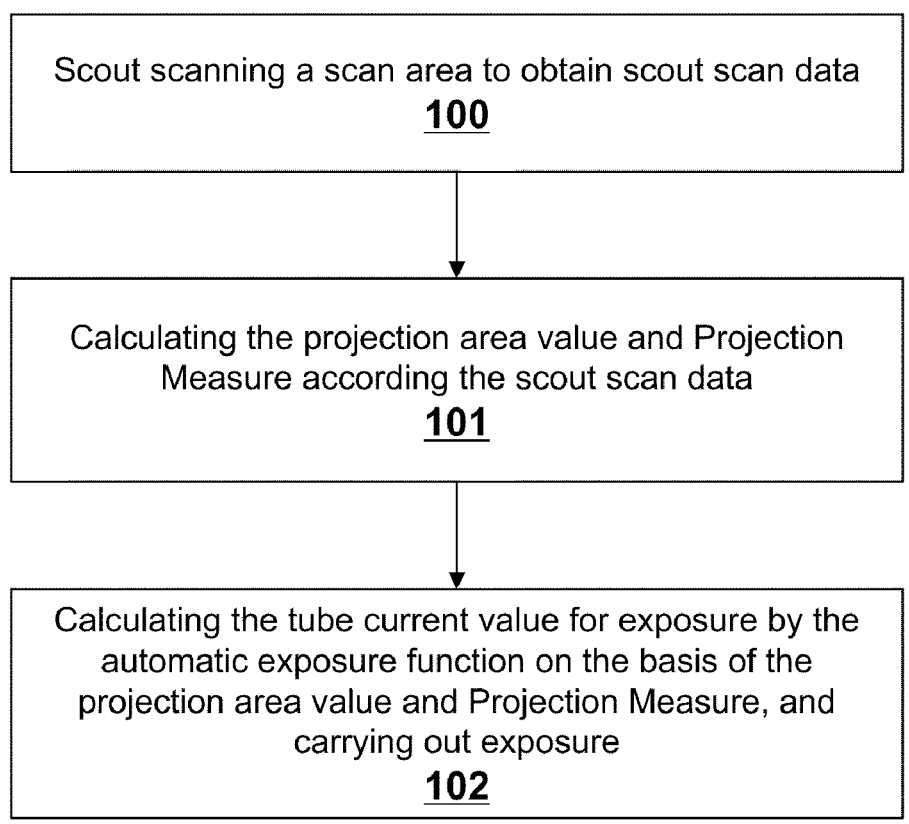
FIG. 1 is a flow chart of the automatic exposure function of the existing X-ray CT system.
Figure 2:
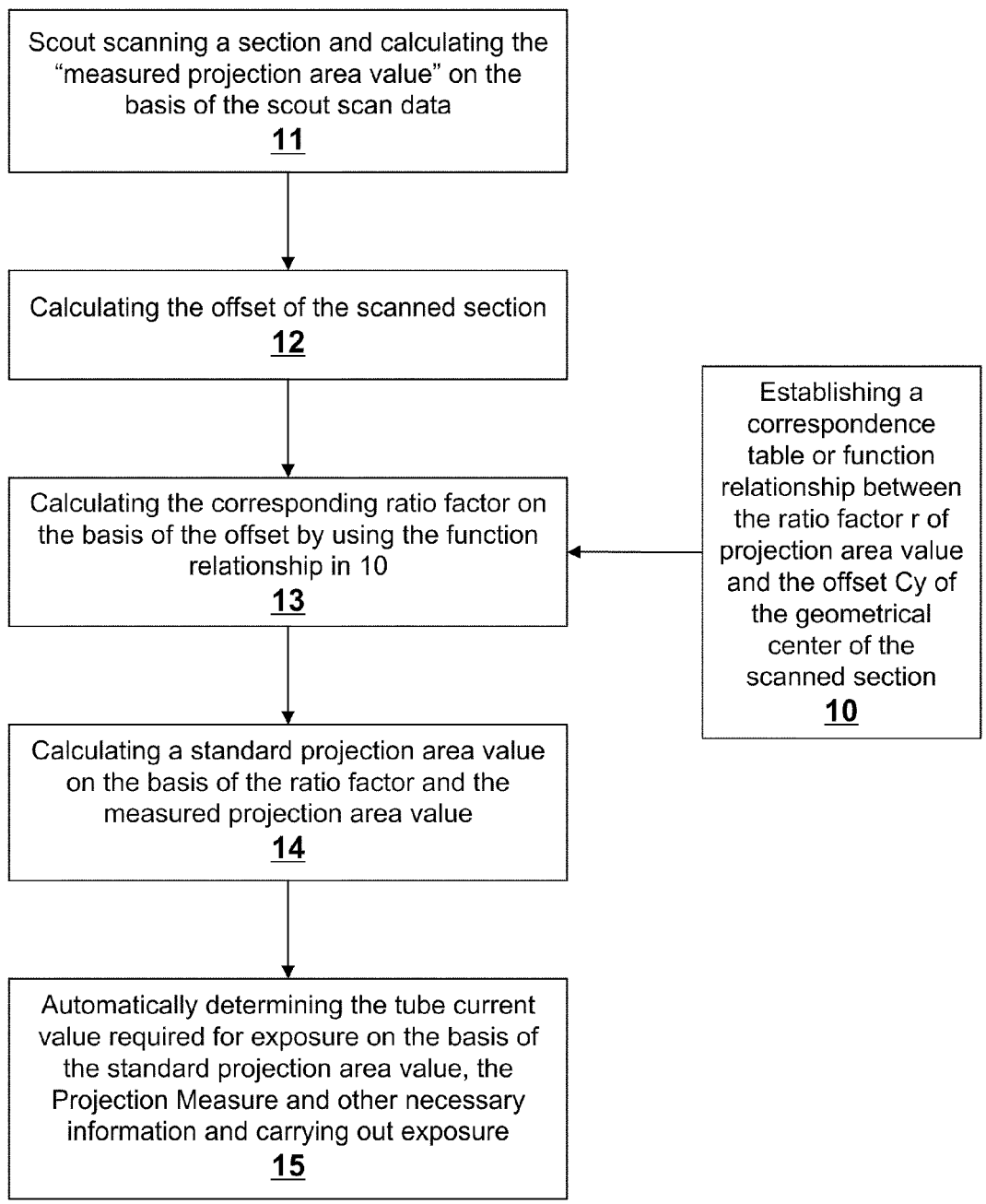
FIG. 2 is a flow chart of the first embodiment of a method for controlling automatic exposure.

FIG. 2 shows the flow chart of a method for controlling automatic exposure of this embodiment which comprises the following steps. A correspondence table or function relationship between the ratio factor r of the projection area value and the offset Cy of the geometrical center of the scanned section is established offline in step 10, wherein the ratio factor r of the projection area value represents a ratio of the projection area value under the situation where the geometrical center of the scanned section of the subject deviates from the rotation center ISO to the standard projection area value under the situation where the geometrical center of the scanned section of the subject locates at the rotation center. In step 11, the subject is scout scanned and the "measured projection area value" and the Projection Measure are calculated based on the scout scan data. In step 12, the offset Cy of the geometrical center of the scanned section from the rotation center ISO is calculated. In step 13, the offset Cy obtained in step 12 is substituted into the correspondence table or function relationship established in step 10 to obtain its corresponding ratio factor r. In step 14, a standard projection area value is calculated on the basis of the ratio factor r and the measured projection area value, and in step 15, the tube current value required for exposure by the automatic exposure function is automatically determined on the basis of the calculated standard projection area value, the Projection Measure and other system parameters, and carrying out exposure.

The calculation of the offset Cy in step 11 can be carried out as following in a first method.

Figure 3:
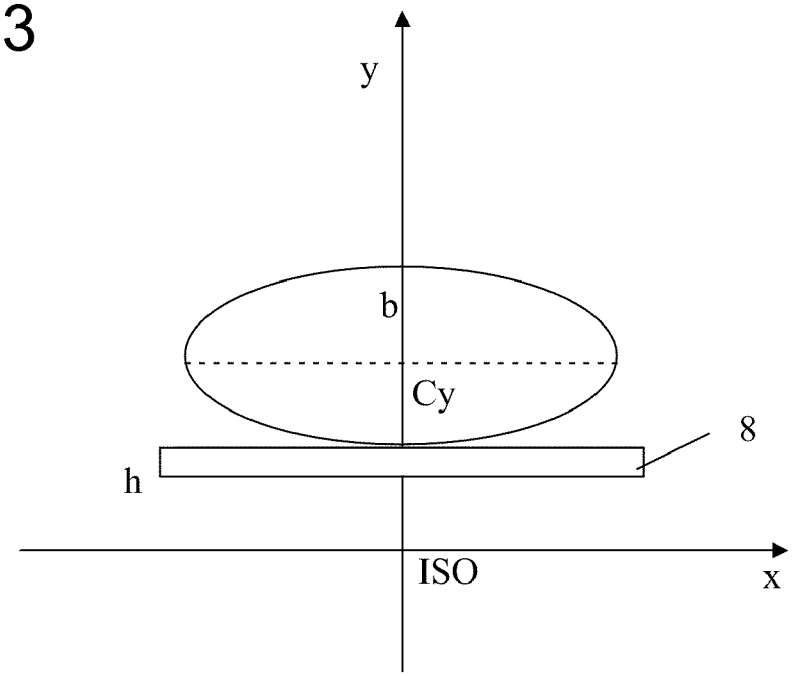
FIG. 3 is a schematic diagram illustrating the calculation of the offset by a first method in the first embodiment.

See FIG. 3 again which is a schematic diagram of a first method that calculates the offset Cy of the geometrical center of the scanned section on the basis of the Projection Measure. It is supposed that the human body is equivalent to a homogenous water body, and then the short axis b of the scanned section of the human body can be derived from the following formula (3):

$$b=k*pm/2 \tag{3}$$

wherein pm is said Projection Measure and k is a constant. The offset Cy is equal to the sum of the short axis b of the scanned section and the distance h of the scan bed 8 from the rotation center ISO, as shown in formula (4):

$$Cy=b+h \tag{4}$$

To make the short axis b of the scanned section more accurate, it can be obtained by establishing a fitting formula (5):

$$b=f(pm)=a0+a1\times pm+a2\times pm^2+a3\times pm^3+ \quad (5)$$

This formula describes the length of the short axis b to be a function in the form of a polynomial that takes pm as the independent variable, wherein a0, a1, a2 and a3 are coefficients in the polynomial.

To improve the adaptability of the formula (5), respective fitting formulas should be established for different tissues such as bone, lung and soft tissue.

In a second method, the offset Cy of the geometrical center of the scanned section is calculated on the basis of the previously scanned image. As the offset Cy changes little substantially along the direction of axis z, a previous tomographic image can be used to predict the offset Cy of said scanned section. First, segmentation is performed on the image of the previous section to determine the contour of the scanned section of the human body. Then, the "average value of the Y-axis coordinates of all the pixel points on the image of the section contour" can be taken as the offset Cy (i.e. the Y-axis coordinates of the geometrical center of the human section).

Figure 4:
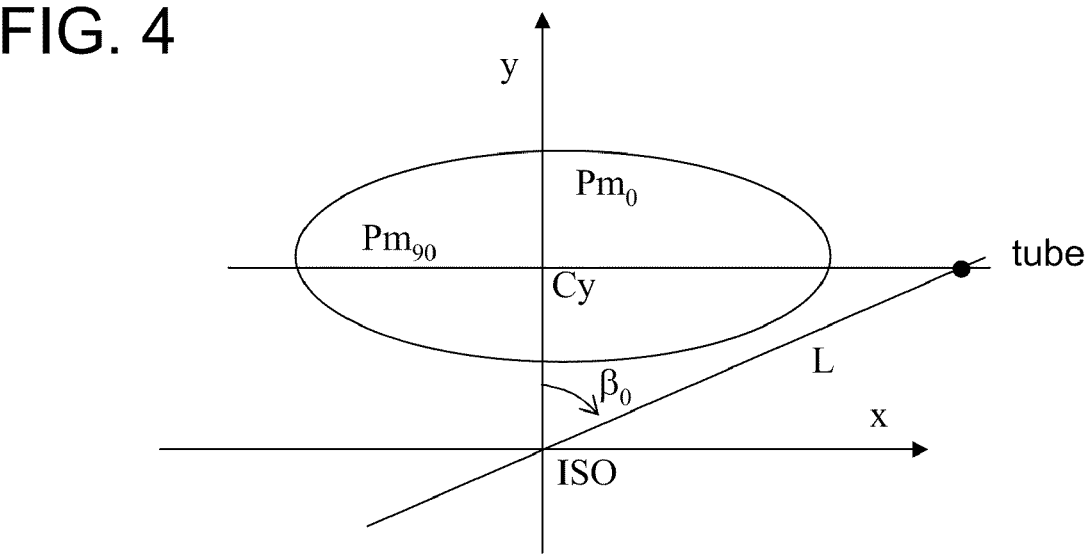
FIG. 4 is a schematic diagram illustrating the calculation of the offset by a second method in the first embodiment.

In the third method, the offset Cy of the geometrical center of the scanned section is calculated on the basis of the projection data of the previous scan. As shown in FIG. 4, all original projection data is collected in the previous axial scan, and the tube rotation angle ($\beta_0$) to which the maximum projection value $p(\beta_0)$ corresponds is found from said projection data. At said rotation angle ($\beta_0$), the tube focus and the central point of the patient are in the same horizontal line. Then the offset Cy of the scanned section can be calculated by the following formula (6):

$$Cy=L*\cos(\beta 0) \quad (6)$$

wherein L is the distance from the tube focus to the rotation center ISO.

Although the above three methods can be used separately to calculate the offset of the geometrical center of the scanned section, they can be used in combination to find the offset of the geometrical center of the scanned section.

The function relationship between the offset Cy and the ratio factor r in step 10 can be obtained by simulation scanning an elliptical phantom of which the long axis, the short axis and the offset are respectively a, b and Cy (or a round phantom of which the radius and the offset are R and Cy respectively) to calculate the projection area value pa(0) in the case of the offset Cy being 0 and the respective projection area values pa(Cy) in the cases of the offset Cy being other than 0; calculating the ratio factor r at respective offset Cy; and creating an index table (Cy, r) to describe the correspondence between Cy and r. The ratio factor r can be expressed in the following formula (7):

$$r=pa(Cy)/pa(0) \quad (7)$$

wherein pa(Cy) represents the projection area value when the offset Cy is not 0 and pa(0) represents the projection area value when the offset Cy is 0.

Figure 5:
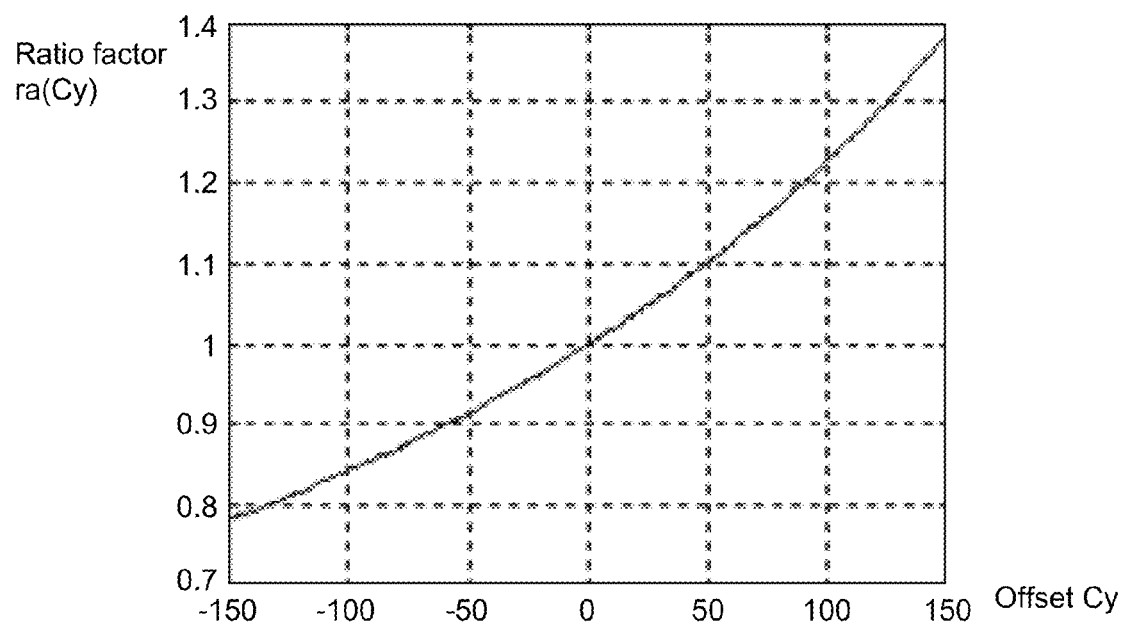
FIG. 5 is a schematic diagram representing the relationship between the ratio factor and the offset in the first embodiment.

In the above simulation examination, the variable Cy is in the range of [−1500, +1500], and the allowed radius R of the round phantom is in the range of [50 mm, 225 mm]. For an elliptical phantom, 10 sets of typical short axis b and elliptical eccentricity (here the eccentricity is defined to be the ratio of the long axis a to the short axis b of the ellipse, and the eccentricity is greater than 1) are set for simulation examination. It is found that the characteristics of the ratio factors r of all the elliptical phantoms and round phantoms are almost identical when the offset Cy is small and the characteristic of the ratio factor r varies greatly when the offset of a large phantom is large (larger than 80 mm). However, if the offset is too large, the phantom may go beyond the maximum field of view (the diameter of conventional field of view is 500 mm). After eliminating the circumstance where the offset causes the phantom to go beyond the maximum field of view, the final result shows that said ratio factor r only relates to the variable Cy and has nothing to do with other factors such as the shape and size of the phantom. FIG. 5 shows the relationship between the ratio factor r and the offset Cy.

The ratio factor r can be obtained not only by looking up the correspondence table established above, but also by such a function as formula (8):

$$r=3.69\times 10^{-6}\times Cy^2+1.946\times 10^{-3}\times Cy+0.999 \quad (8).$$

When actually scanning a patient, the ratio factor r can be obtained upon the determination of the variable offset Cy, and then the standard projection area value, namely the projection area value when the offset is 0, can be obtained from the formula (7), i.e.

$$\text{Standard}\_pa=pa(Cy=0)=pa(Cy)/r.$$

Table 1 shows the application of the first embodiment of the present invention wherein a polyethylene phantom B3 is scanned four times. First, the phantom B3 is placed at the rotation center ISO and is scout scanned at 0 degree and 180 degree, and corresponding projection area values are recorded. Then the phantom B3 is placed 60 mm below the rotation center ISO and scout scanned at 0 degree and 180 degree, and corresponding projection area values are recorded. Ratio factors to which offsets of +60 mm and −60 mm correspond can be looked up from Table 1, and the standard projection area values in the respective positions can be calculated. It can be seen from Table 1 that the standard projection area value thus calculated has an error less than 1.5% as compared to the actual projection area value obtained when the phantom is at the rotation center, and the errors in the range between ±2% are acceptable for all scanned phantoms.

TABLE 1

| Cy | pa(Cy) | ra(Cy) | pa(Cy = 0) | error (%) |
| --- | --- | --- | --- | --- |
| 0 | 2278.32 | 1 | | |
| 60 mm | 2527.4 | 1.1228 | 2250.979694 | −1.20002 |
| 0 | 2197.29 | 1 | | |
| −60 mm | 2001.49 | 0.8983 | 2228.086385 | 1.401562 |

Figure 6:
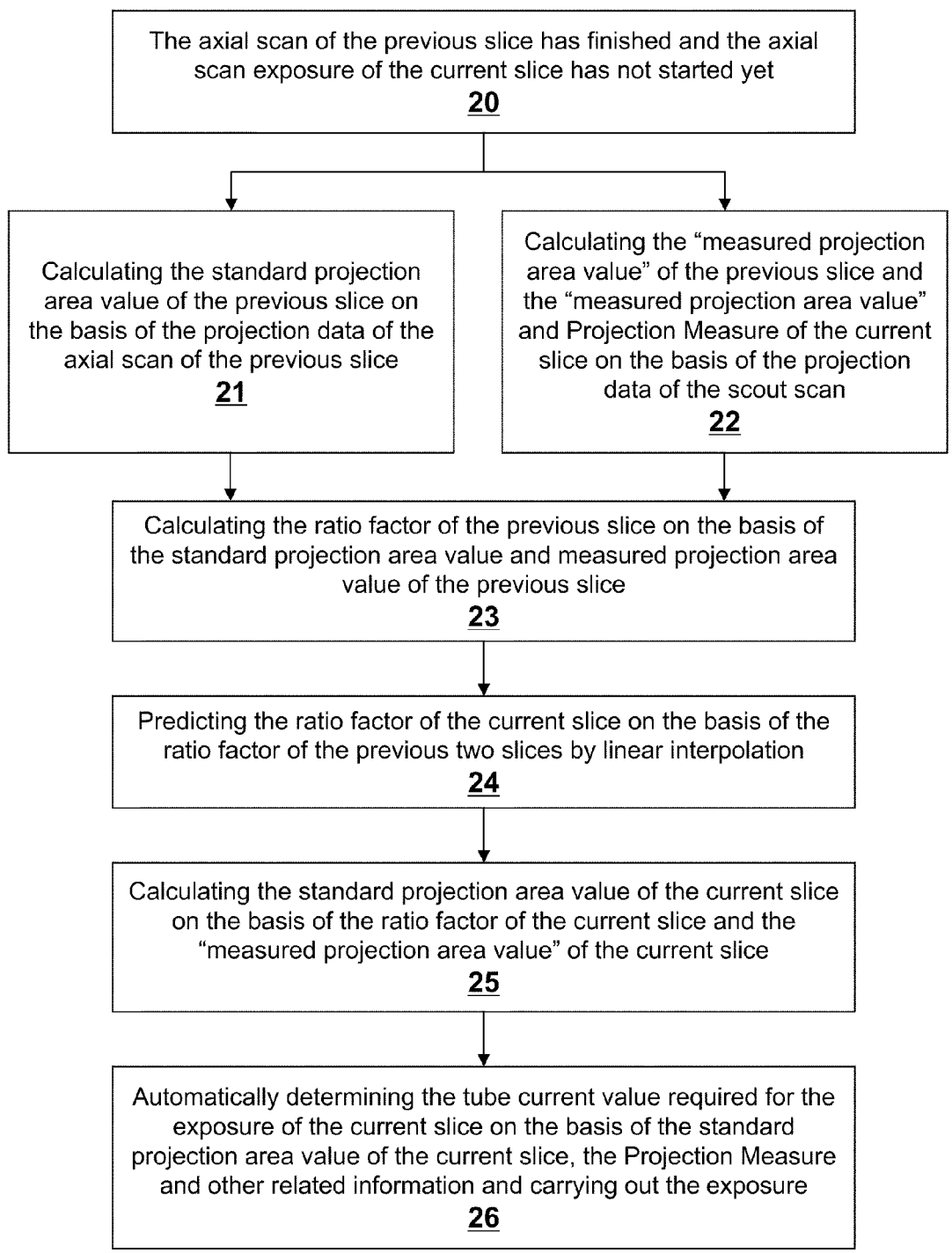
FIG. 6 is a flow chart of the second embodiment of the method for controlling automatic exposure.

FIG. 6 is a flow chart of a second embodiment of the present invention for performing the automatic exposure control function. This embodiment calibrates in real-time the tube current required for the exposure of the current scanned section in an on-line manner. First, a scout scan is performed on the area to be scanned to obtain the scout scan data of the scanned section.

In step 20 the axial scan of the previous scan has finished but the axial scan exposure of the current slice has not started yet. In step 21 the standard projection area value of said previous slice is calculated on the basis of the projection data of the axial scan of the previous slice. In step 22 the "measured projection area value" of the previous slice and the "measured projection area value" and Projection Measure of the current slice are calculated on the basis of the projection data of the scout scan. In step 23 the ratio factor ra(Cy) of the previous slice is calculated on the basis of the standard projection area value and measured projection area value of the previous slice obtained respectively in steps 21 and 22, wherein in this embodiment said ratio factor ra(Cy) of the previous slice is the ratio of the standard projection area value to the measured projection area value, and certainly another way of expression can also be adopted, such as a ratio of the measured projection area value to the standard projection area value. In step 24 the ratio factor of the current slice is predicted on the basis of the ratio factor of the previous two slices by linear interpolation. In step 25 the predicted standard projection area value of the current slice is calculated on the basis of the ratio factor of the current slice calculated in step 24 and the measured projection area value of the current slice calculated in step 22. In step 26 the automatic exposure function of the CT system automatically determines the tube current value required for the exposure of the current slice on the basis of the predicted standard projection area value of the current slice, the Projection Measure and related system parameters, and carries out the exposure.

The standard projection area value of the previous slice (hereinafter represented by #(i−1)) can be obtained in step 21 by calculating the projection area value (pa(i−1,Cy)) of the previous slice #(i−1) at the offset (Cy) and the Projection Measure $pm_0$ (related to the length of the short axis) when the tube is at 0 degree on the basis of the scout scan data during the scanning process of the previous slice #(i−1) in which the patient is placed at Cy. Returning to FIG. 4, the third method for calculating the offset in the embodiment 1 is used for finding the tube rotation angle $\beta_0$ to which the maximum projection data value $P(\beta_0)$ corresponds. At the rotation angle $\beta_0$, the X-ray at the channel having a fan-beam flare angle of $((\pi/2-\beta_0))$ with respect to the central channel passes through the long axis of the elliptical slice being scanned, so information relating to the long axis of said ellipse can be obtained on the basis of the Projection Measure $pm_{90}$ at said rotation angle $\beta_0$. Then the standard projection area value (pa(i−1,Cy=0)) of said slice #(i−1) at the offset Cy=0 can be calculated according to formula (9):

$$pa(i-1,Cy=0)=pm_0*pm_{90}*S+I \quad (9),$$

wherein S and I are constants.

The ratio factor ra(i−1) of the previous slice in step 23 can be expressed using the following formula (10):

$$ra(i-1)=pa(i-1,Cy=0)/pa(i-1,Cy) \quad (10),$$

wherein pa(i−1,Cy) is the measured projection area value calculated on the basis of the projection data of the scout scan in step 22 when the previous slice #(i−1) is at the offset Cy.

The ratio factor ra(i) of the current slice #i can be obtained in said step 24 by extrapolation, and in this embodiment it is obtained by linear extrapolation, such as by the following formula (11):

$$ra(i)=2\times ra(i-1)-ra(i-2) \quad (11),$$

wherein ra(i−2) represents the ratio factor of the slice #(i−2).

The standard projection area value pa(i,Cy=0) of the current slice can be obtained in step 25 through the following formula (12):

$$pa(i,Cy=0)=pa(i,Cy)*ra(i) \quad (12),$$

wherein pa(i,Cy) is the "measured projection area value" of the current slice calculated on the basis of the projection data of the scout scan in step 22.

In step 26, the automatic exposure control function can automatically determine the tube current required for exposing the current slice on the basis of the calculated standard projection area value pa(i,Cy=0) of the current slice, the Projection Measure and other system parameters (such as the expected image noise), and carry out the exposure.

This embodiment controls the tube current required for exposure by converting the fan-shaped beam into parallel beam projection. With respect to a parallel beam, the sums of the projection values of all channels in each parallel direction are identical. In other words, once the projection area value is defined as the sum of the projection values of all channels in one parallel direction, then it will not be affected by the offset of the subject. In this embodiment, the projection area value is defined as the sum of the projection values of all channels in one parallel direction.

Figure 7:
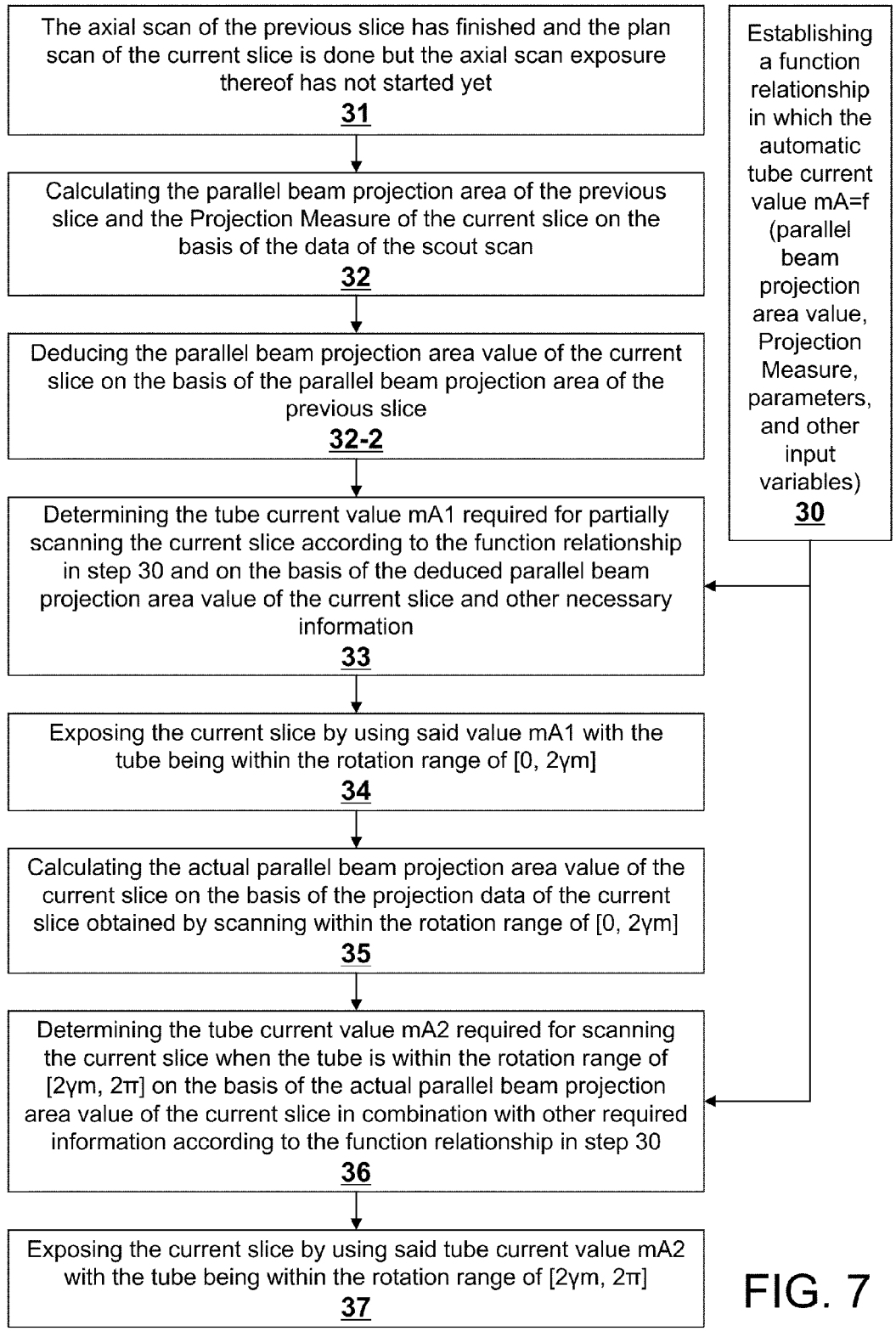
FIG. 7 is a flow chart of the third embodiment of the method for controlling automatic exposure.

FIG. 7 is a flow chart of the third embodiment of the present invention for performing the automatic exposure control function.

In step 30 a function relationship is established between the automatic tube current value mA and the parallel beam projection area value and Projection Measure, namely mA=f (parallel beam projection area value, Projection Measure, system parameters, and other input variables), wherein the system parameters and other input variables are intrinsic to the system or are input by the operator as required. In step 31 the axial scan of the previous slice has finished but the axial scan exposure of the current slice has not started yet. In step 32 the parallel beam projection area value of the previous slice is calculated on the basis of the projection data of the axial scan of the previous slice. In step 32-2 the parallel beam projection area value of the current slice is deduced on the basis of the parallel beam projection area value(s) of the previous one or two slices. In step 33 the tube current value mA1 required for partially scanning the current slice is determined according to the function relationship established in step 30 and on the basis of the deduced parallel beam projection area value of the current slice and other necessary information. In step 34 an exposure is performed by using said mA1 value with the tube being in the rotation range of [0, $2\gamma_m$], wherein said $\gamma_m$ is half the fan-shaped flare angle of the X-ray beam. In step 35 the actual parallel beam projection area value of the current slice is calculated on the basis of the projection data of the current slice obtained by the scanning in step 34 where the tube is within the rotation range of [0, $2\gamma_m$]. In step 36 the parallel beam projection area value of the current slice calculated in step 35 and other system parameters are substituted into the function relationship established in step 30, and the tube current value mA2 required for scanning the current slice when the tube is within the rotation range of [$2\gamma_m$, $2\pi$] are determined. In step 37 an exposure is performed by using said tube current value mA2 with the tube being within the rotation range of [$2\gamma_m$, $2\pi$].

The method for obtaining the parallel beam projection area in the third embodiment includes, in step 1, converting the fan-shaped beam projection into parallel beam projection by interpolation or beam rebinning. In step 2, equidistant processing is performed by interpolation on the parallel beams obtained in step 1 to obtain equidistant parallel beam projection, and, in step 3, the sum of the projection values of channels of all equidistant parallel beams is calculated, with said sum being the parallel beam projection area value.

Figure 8:
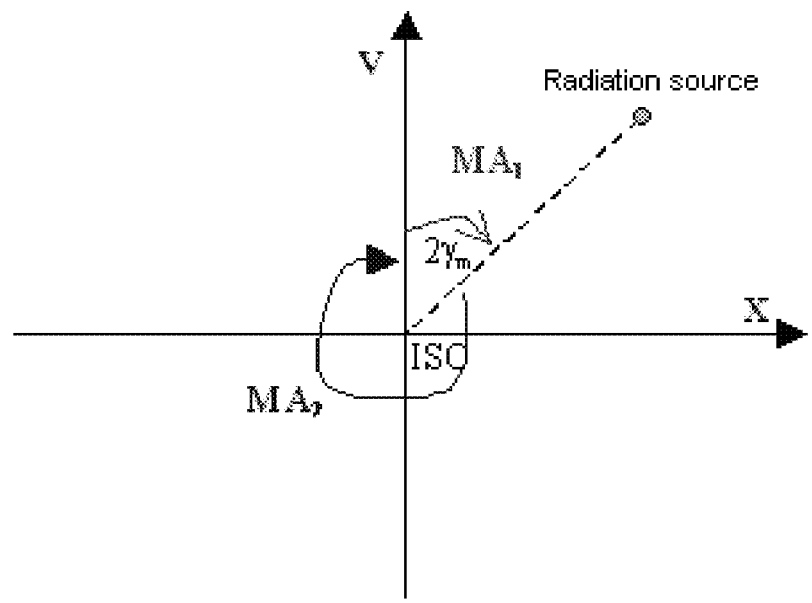
FIG. 8 is a schematic diagram of two tube current values in one scanning rotation in the third embodiment.

See FIG. 8. In the method of this embodiment, during the scanning of the current slice #i, two different tube current values mA1 and mA2 are used for exposure with respect to two different tube rotation angular ranges of [0, $2\gamma_m$] and [$2\gamma_m$, $2\pi$] respectively.

The parallel beam projection area value ppa(i) of the current slice #i can be obtained in step 32-2 by extrapolation (e.g. the linear extrapolation such as formula (11)) on the basis of the parallel beam projection area values ppa(i−1) and ppa(i−

2) of the previous two slices #(i−1) and #(i−2). A simpler way is to take ppa(i−1) as ppa(i) (hold processing). Substituting the estimated parallel beam projection area value ppa(i) of the current slice #i and the Projection Measure into the function relationship established in step 30 can generate the tube current value mA1 required for exposing the current slice. The tube current value mA1 is suitable for use in exposure only when the current slice #i is scanned with the tube being within the rotation range of $[0, 2\gamma_m]$.

Figure 9:
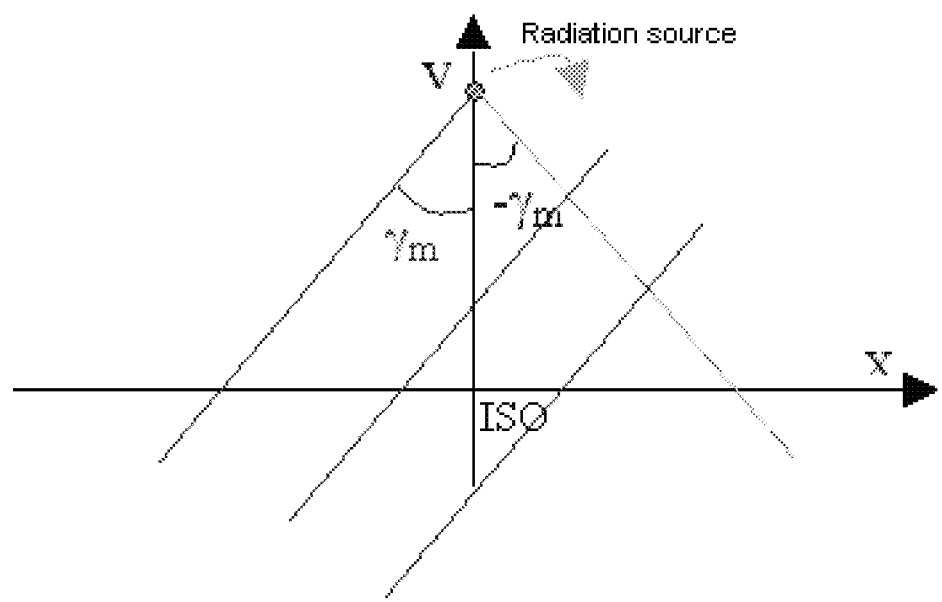
FIG. 9 and FIG. 10 are schematic diagrams illustrating how to find the unique parallel rays for calculating the parallel beam projection area value in the third embodiment of the present invention.
Figure 10:
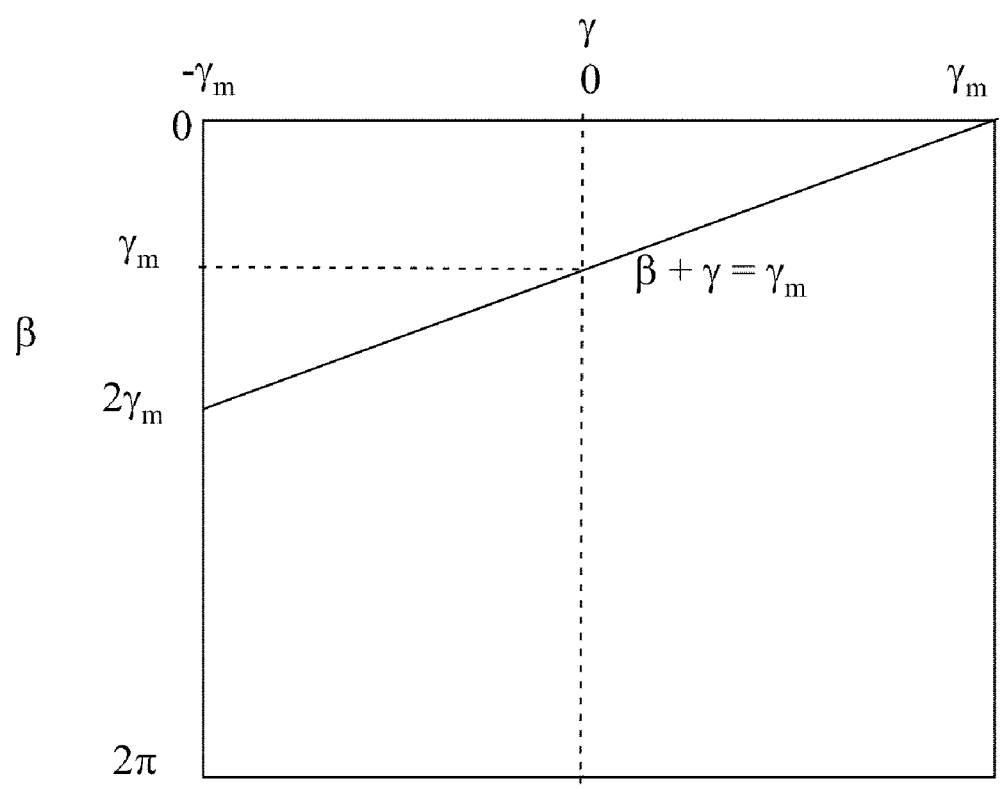

As is shown in FIG. 9 and FIG. 10, the actual parallel beam projection area value of the current slice #i can be obtained in step 35 by first collecting all projection data of the current slice #i when the rotation angle of the tube is in the range of $[0, 2\gamma_m]$; then finding a group of unique parallel beams which have an angle $\gamma_m$ with respect to Y-axis, wherein $\gamma_m$ can be expressed in the formula (14):

$$\beta + \gamma = \gamma_m \qquad (14)$$

wherein $\beta$ represents the rotation angle of the tube, and $\gamma$ represents the fan-shaped flare angle of the beam of a certain channel with respect to the central channel; and calculating the actual parallel beam projection area value ppa(i) of the current slice #i on the basis of said parallel beams.

In this embodiment, the tube current value can be converted from mA1 to mA2 smoothly by modulation or filtering, taking into account the responding speed of the tube and the high voltage generator.

What is claimed is:

1. A method for controlling automatic X-ray exposure in an X-ray CT system, said method comprising:
    establishing one of a correspondence table and a function relationship between a ratio factor r and an offset Cy of a geometrical center of a scanned section, wherein the ratio factor r represents a ratio of a projection area value when the geometrical center of the scanned section of a subject deviates from a rotation center to a standard projection area value when the geometrical center of the scanned section of the subject is located at the rotation center;
    scout scanning the subject and calculating a "measured projection area value" and a Projection Measure based on data obtained in the scout scan;
    calculating the offset Cy of the geometrical center of the scanned section from the rotation center by:
        supposing that a human body is equivalent to a homogenous water body; and
        deriving a short axis b of a scanned section of the human body from the following formula:

$$b = k*pm/2,$$

wherein pm is the Projection Measure and k is a constant, with the offset Cy being equal to a sum of the short axis b of the scanned section and a distance of a scan table from the rotation center;
    substituting the offset Cy into one of the correspondence table and function relationship to obtain its corresponding ratio factor r;
    calculating the standard projection area value based on the ratio factor r and the measured projection area value; and
    automatically determining by automatic exposure function a tube current value required for exposure based on the calculated standard projection area value, the Projection Measure, and carrying out exposure.

2. The method for controlling automatic X-ray exposure in an X-ray CT system according to claim 1, further comprising obtaining the short axis b of the scanned section using the following fitting polynomial formula:

$$b = f(pm) = a0 + a1 \times pm + a2 \times pm2 + a3 \times pm3 + \ldots,$$

wherein a0, a1, a2, and a3 are coefficients in the polynomial.

3. A method for controlling automatic X-ray exposure in an X-ray CT system, said method comprising:
    establishing one of a correspondence table and a function relationship between a ratio factor r and an offset Cy of a geometrical center of a scanned section, wherein the ratio factor r represents a ratio of a projection area value when the geometrical center of the scanned section of a subject deviates from a rotation center to a standard projection area value when the geometrical center of the scanned section of the subject is located at the rotation center;
    scout scanning the subject and calculating a "measured projection area value" and a Projection Measure based on data obtained in the scout scan;
    calculating the offset Cy of the geometrical center of the scanned section from the rotation center by:
        collecting all original projection data in a previous axial scan;
        finding from the projection data a tube rotation angle $\beta_0$ to which a maximum projection value $P(\beta_0)$ corresponds and at which a tube focus and a central point of the subject are in a same horizontal line; and
        calculating the offset Cy of the scanned section according to the following formula:

$$Cy = L * \cos(\beta 0),$$

wherein L is a distance from the tube focus to the rotation center;
    substituting the offset Cy into one of the correspondence table and function relationship to obtain its corresponding ratio factor r;
    calculating the standard projection area value based on the ratio factor r and the measured projection area value; and
    automatically determining by automatic exposure function a tube current value required for exposure based on the calculated standard projection area value, the Projection Measure, and carrying out exposure.

4. A method for controlling automatic X-ray exposure in an X-ray CT system, said method comprising:
    establishing one of a correspondence table and a function relationship between a ratio factor r and an offset Cy of a geometrical center of a scanned section, wherein the ratio factor r represents a ratio of a projection area value when the geometrical center of the scanned section of a subject deviates from a rotation center to a standard projection area value when the geometrical center of the scanned section of the subject is located at the rotation center, wherein the function relationship between the offset Cy and the ratio factor r is expressed as the following:

$$r = 3.69 \times 10^{-6} \times Cy^2 + 1.946 \times 10^{-3} \times Cy + 0.999;$$

scout scanning the subject and calculating a "measured projection area value" and a Projection Measure based on data obtained in the scout scan;
    calculating the offset Cy of the geometrical center of the scanned section from the rotation center;
    substituting the offset Cy into one of the correspondence table and function relationship to obtain its corresponding ratio factor r;
    calculating the standard projection area value based on the ratio factor r and the measured projection area value; and
    automatically determining by automatic exposure function a tube current value required for exposure based on the calculated standard projection area value, the Projection Measure, and carrying out exposure.

5. A method for controlling automatic X-ray exposure in an X-ray CT system, which is carried out in such a situation that a scout scan has been performed on a scan area to obtain scout scan data of a scanned section and an axial scan of a previous slice has finished but an axial scan of a current slice has not started yet, said method comprising:

calculating a standard projection area value of the previous slice based on the projection data of the axial scan of the previous slice;

calculating a "measured projection area value" of the previous slice and a "measured projection area value" and Projection Measure of the current slice based on the scout scan data;

calculating a ratio factor ra(Cy) of the previous slice based on the standard projection area value and the measured projection area value of the previous slice, wherein the ratio factor ra(Cy) of the previous slice is a ratio of the standard projection area value to the measured projection area value;

predicting the ratio factor of the current slice based on the ratio factor of the two previous slices using linear interpolation;

calculating a predicted standard projection area value of the current slice based on the ratio factor of the current slice and the measured projection area value of the current slice; and automatically determining a tube current value required for exposing the current slice using an automatic exposure function of the CT system based on the predicted standard projection area value of the current slice, the Projection Measure, and carrying out the exposure.

6. The method for controlling automatic X-ray exposure in an X-ray CT system according claim 5, wherein calculating a standard projection area value of the previous slice comprises:

calculating the projection area value (pa(i−1,Cy)) of the previous slice at an offset (Cy) and the Projection Measure ($pm_0$) when a tube is at 0 degree based on the scout scan data during the scanning process of the previous slice, wherein Cy is the offset of a patient from a rotation center of the CT system;

finding a tube rotation angle ($\beta_0$) to which a maximum projection data value P($\beta_0$) corresponds, and thus finding the Projection Measure ($pm_{90}$) at the rotation angle ($\beta_0$), because at the rotation angle ($\beta_0$), an X-ray at a particular channel that has a fan-beam flare angle of (($\pi/2-\beta_0$)) with respect to a central channel passes through a long axis of a scanned elliptical slice; and calculating the standard projection area value (pa(i−1, Cy=0)) of the previous slice at an offset (Cy) of 0 by the following formula:

$$pa(i-1,Cy=0)=pm_0 * pm_{90} * S + I,$$

wherein (i−1) represents the previous slice and S and I are constants.

7. The method for controlling automatic X-ray exposure in an X-ray CT system according claim 5, wherein predicting a ratio factor of the previous slice comprises predicting the ratio factor using extrapolation.

8. The method for controlling automatic X-ray exposure in an X-ray CT system according claim 5, wherein calculating a measured projection area value of the current slice and calculating a measured projection area value of the previous slice are each based on the scout scan data.

9. A method for controlling automatic X-ray exposure in an X-ray CT system, which is to be carried out after an axial scan of a previous slice has been finished but an axial scan exposure of a current slice has not began, said method comprising:

establishing a function relationship between an automatic tube current value mA, a parallel beam projection area value, and a Projection Measure;

calculating a parallel beam projection area value of the previous slice based on the projection data of the axial scan of the previous slice;

deducing a parallel beam projection area value of the current slice based on the parallel beam projection area value of the previous slice;

determining a first tube current value mA1 required for partially scanning the current slice according to the function relationship established and based on the deduced parallel beam projection area value of the current slice;

performing exposure by using the first tube current value mA1 when a tube is in a first rotation range of [0, $2\gamma_m$], wherein γm is half of a fan-shaped flare angle of an X-ray beam;

calculating an actual parallel beam projection area value of the current slice based on the projection data of the current slice where the tube is within the first rotation range of [0, $2\gamma_m$];

substituting the parallel beam projection area value of the current slice into the function relationship, and determining a second tube current value mA2 required for scanning the current slice when the tube is within a second rotation range of [$2\gamma_m$, $2\pi$]; and performing exposure using the second tube current value mA2 with the tube being in the second rotation range of [$2\gamma_m$, $2\pi$].

10. The method for controlling automatic X-ray exposure in an X-ray CT system according claim 9, further comprising obtaining the parallel beam projection area by:

converting the fan-shaped beam projection into parallel beam projection by one of interpolation and beam rebinning;

performing, by way of interpolation, equidistant processing on the parallel beam to obtain equidistant parallel beam projection; and calculating a sum of projection values of each channel of all the equidistant parallel beams, the sum being the parallel beam projection area value.

11. The method for controlling automatic X-ray exposure in an X-ray CT system according claim 9, wherein the parallel beam projection area value of the current slice is equal to the parallel beam projection area value of the previous slice, said method further comprising substituting the estimated parallel beam projection area value of the current slice and the Projection Measure into the function relationship to generate the first tube current value mA1 required for exposing the current slice, wherein the first tube current value mA1 is applicable for exposing the current slice only when the tube is within the first rotation range of [0, $2\gamma_m$].

12. The method for controlling automatic X-ray exposure in an X-ray CT system according claim 9, wherein calculating an actual parallel beam projection area value of the current slice comprises:

collecting all projection data of the current slice when the tube is within the first rotation angle range of [0, $2\gamma_m$];

finding a group of unique parallel beams which have an angle of $\gamma_m$ with respect to Y-axis with $\gamma_m$ satisfying the following formula:

$$\beta + \gamma = \gamma_m,$$

wherein β represents the rotation angle of the tube and γ represents the fan-shaped flare angle of the beam of a certain channel with respect to the central channel; and calculating the actual parallel beam projection area value of the current slice based on the parallel beams found above.

* * * * *